US008668639B2

(12) United States Patent
Kagaya et al.

(10) Patent No.: US 8,668,639 B2
(45) Date of Patent: Mar. 11, 2014

(54) IMAGE OBTAINMENT METHOD AND APPARATUS

(75) Inventors: Makoto Kagaya, Kanagawa-ken (JP); Issei Suzuki, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 175 days.

(21) Appl. No.: 13/411,421

(22) Filed: Mar. 2, 2012

(65) Prior Publication Data

US 2012/0226102 A1 Sep. 6, 2012

(30) Foreign Application Priority Data

Mar. 3, 2011 (JP) ................................. 2011-046056

(51) Int. Cl.
*A61B 1/06* (2006.01)
*A61B 1/045* (2006.01)
*A61B 1/00* (2006.01)

(52) U.S. Cl.
CPC . *A61B 1/06* (2013.01); *A61B 1/045* (2013.01); *A61B 1/00006* (2013.01)
USPC .............................. 600/180; 600/178; 348/68

(58) Field of Classification Search
CPC ....... A61B 1/06; A61B 1/045; A61B 1/00006
USPC ................. 600/178, 180; 348/68, 69
See application file for complete search history.

(56) References Cited

U.S. PATENT DOCUMENTS

| 5,608,451 | A * | 3/1997 | Konno et al. ................... 348/69 |
| 6,078,353 | A | 6/2000 | Yamanaka et al. |
| 6,413,207 | B1 * | 7/2002 | Minami ......................... 600/109 |
| 6,734,894 | B1 * | 5/2004 | Higuchi et al. .................. 348/69 |
| 2003/0202090 | A1 * | 10/2003 | Ota et al. ......................... 348/69 |
| 2007/0112253 | A1 * | 5/2007 | Negishi ......................... 600/118 |
| 2009/0036743 | A1 * | 2/2009 | Yabe et al. ..................... 600/180 |
| 2012/0016201 | A1 * | 1/2012 | Seto et al. ..................... 600/180 |
| 2012/0123213 | A1 * | 5/2012 | Seto ............................. 600/178 |

OTHER PUBLICATIONS

Extended European Search Report dated May 24, 2012.

\* cited by examiner

*Primary Examiner* — John P Leubecker
(74) *Attorney, Agent, or Firm* — McGinn IP Law Group, PLLC

(57) ABSTRACT

In an image-obtainment-apparatus that obtains an image of an observation-region by imaging, by an imaging-device, light output from the observation-region illuminated with illumination-light, when the light-amount of the illumination-light illuminated the observation-region is less than or equal to first-threshold-value, the electronic-shutter-speed is controlled at first-constant-speed, and the light-amount of the illumination-light is controlled based on the light-amount of the illumination-light illuminated the observation-region. When the light-amount of the illumination-light illuminated the observation-region is greater than first-threshold-value and less than or equal to second-threshold-value, the electronic-shutter-speed is controlled at a speed based on the light-amount of the illumination-light illuminated the observation-region, and the light-amount of the illumination-light is controlled at a predetermined constant light-amount. When the light-amount of the illumination-light illuminated the observation-region is greater than second-threshold-value, the electronic-shutter-speed is controlled at second-constant-speed, and the light-amount of the illumination-light is controlled based on the light-amount of the illumination-light illuminated the observation-region.

11 Claims, 10 Drawing Sheets

| SCOPE INFORMATION | SECOND CONSTANT SPEED |
|---|---|
| S1 | SV1 |
| S2 | SV2 |
| S3 | SV3 |
| ⋮ | ⋮ |

| USER INFORMATION | SECOND CONSTANT SPEED |
|---|---|
| ID1 | SV4 |
| ID2 | SV5 |
| ID3 | SV6 |
| ⋮ | ⋮ |

IMAGE OBTAINMENT METHOD AND APPARATUS

BACKGROUND OF THE INVENTION

1. Field of the Invention

The present invention relates to an image obtainment method apparatus for obtaining an image of a region to be observed by illuminating the region to be observed with illumination light output from a light source, and by imaging, by an imaging device, light output from the region to be observed by illumination with the illumination light. In particular, the present invention relates to control of the light amount of illumination light, and control of the electronic shutter speed of the imaging device.

2. Description of the Related Art

Conventionally, endoscope systems for observing tissue in a patient's body are widely known. Further, electronic endoscope systems that obtain a visible image of a region to be observed in a patient's body by imaging the region to be observed by an imaging device, and that display the obtained image on a monitor screen are widely used.

Such endoscope systems perform short-distance imaging, long-distance imaging, and the like. In short-distance imaging, a leading end of an insertion unit of an endoscope system, which is inserted into a patient's body, is placed close to a lesion or the like to image the lesion or the like. In long-distance imaging, a relatively wide range including a lesion and the vicinity thereof is imaged.

For example, when the light amount of illumination with which a region to be observed is illuminated is constant, relatively bright image signals are obtained in short-distance imaging, because a distance between the lending end of the insertion unit and the lesion is short. However, in long-distance imaging, relatively dark image signals are obtained, for example, when the inside of an intestine is imaged, because the target of imaging is tubular. Therefore, there is a problem that visible images displayed on a monitor are too light or too dark in some cases.

Therefore, a method for automatically changing the light amount of illumination light based on the luminance component or the like of image signals obtained by an imaging device so that the brightness (luminance) of visible images displayed on the monitor becomes constant has been proposed. Specifically, the light amount of illumination light is automatically reduced, as the luminance component of image signals obtained by the imaging device is larger, and the light amount of illumination light is automatically increased, as the luminance component of image signals obtained by the imaging device is smaller.

However, the light amount of illumination light output from a light source is limited, and the variation range of the aperture of a diaphragm for adjusting the light amount of illumination light output from the light source is limited, because of the mechanical precision and accuracy of an apparatus, or the like. Therefore, the brightness of visible images is not maintained at a constant level in some cases.

Meanwhile, in the aforementioned endoscope systems, dynamic image (video) imaging is performed by performing real-time imaging by the imaging device. Further, a still image is obtainable by obtaining a desirable frame from a series of frames of visible images obtained by dynamic image imaging.

Since the still image is obtained especially to perform precise observation, it is desirable that a blur in the still image is minimized. Therefore, it is desirable that the electronic shutter speed of the imaging device is as high as possible.

For example, U.S. Pat. No. 6,078,353 (Patent Document 1) proposes a method in which sufficiently bright visible images are obtained by setting a low electronic shutter speed of the imaging device when the aperture of a light source is fully open, in other words, when a region to be observed is dark. In contrast, when the aperture of the light source is not fully open, in other words, when the region to be observed is light, a high electronic shutter speed is set.

However, Patent Document 1 proposes switching the electronic shutter speed only to three levels, namely, $1/60$ second, $1/200$ second, and $1/400$ second, depending on whether the aperture of the light source is fully open or not. If the electronic shutter speed is switched only to these three levels, it is still impossible to maintain a constant brightness of visible images in some cases. In such cases, unpleasant visible images are provided for observers, and there is a risk of imposing a burden on the observers.

Further, in Patent Document 1, after the electronic shutter speed is set to one of the three speeds, the brightness is adjusted mainly by changing the aperture of the light source. However, for example, when the frame rate of the imaging device is high, and the light amount needs to be adjusted at high speed by changing the aperture, a highly accurate mechanism that can provide high response speed and highly accurate adjustment of the position of the aperture is necessary. Therefore, the mechanism for controlling the light amount becomes complicated, and that causes an increase in the cost of the system.

SUMMARY OF THE INVENTION

In view of the foregoing circumstances, it is an object of the present invention to provide an image obtainment method and apparatus that can maintain a constant brightness of visible images more appropriately, and reduce a blur in still images without using a complicated mechanism.

An image obtainment method of the present invention is an image obtainment apparatus comprising:

an illumination light illuminating unit that illuminates a region to be observed with illumination light output from a light source;

an image obtainment unit that obtains an image of the region to be observed by imaging, by an imaging device, light output from the region to be observed by illumination with the illumination light;

a light amount control unit that controls the light amount of the illumination light output from the light source; and an electronic shutter speed control unit that controls the electronic shutter speed of the imaging device, wherein the electronic shutter speed control unit controls the electronic shutter speed at a first constant speed, and the light amount control unit controls the light amount of the illumination light output from the light source based on the light amount of the illumination light with which the region to be observed has been illuminated, when the light amount of the illumination light with which the region to be observed has been illuminated is less than or equal to a first threshold value, and wherein the electronic shutter speed control unit controls the electronic shutter speed at a speed based on the light amount of the illumination light with which the region to be observed has been illuminated, and the light amount control unit controls the light amount of the illumination light output from the light source at a predetermined constant light amount, when the light amount of the illumination light with which the region to be observed has been illuminated is greater than the first threshold value and less than or equal to a second threshold value that is larger than the first threshold value, and wherein the electronic shutter speed control unit controls the electronic shutter speed at a second constant speed that is higher than the first constant speed, and the light amount control unit controls the light amount of the illumination light output from the light source based on the light amount of the illumination light with which the region to be observed has been illuminated, when the light amount of the illumination light with which the region to be observed has been illuminated is greater than the second threshold value.

In the image obtainment apparatus of the present invention, the light amount control unit may obtain an up-to-latest-time history of the light amount of the illumination light output from the light source (the term "up-to-latest-time history" means a history up to a time point immediately before this operation is performed by the light amount control unit), and change the predetermined constant light amount based on the obtained up-to-latest-time history of the light amount.

The image obtainment apparatus of the present invention may further include a scope unit that is inserted into a patient's body (the body of a person to be examined) to guide the illumination light output from the light source to illuminate the region to be observed with the illumination light, and to receive the light output from the region to be observed, and the scope unit being provided in a detachable manner, and a scope information obtainment unit that obtains information representing the kind of the scope unit. Further, the electronic shutter speed control unit may set the second constant speed based on the information representing the kind of the scope unit obtained by the scope information obtainment unit.

The information representing the kind of the scope unit may include information representing the kind of the imaging device.

The information representing the kind of the scope unit may include information about the maximum light amount of the illumination light that is receivable by the scope unit.

Further, the image obtainment apparatus of the present invention may further include a scope information receiving unit that receives an input of the information representing the kind of the scope unit, and the scope information obtainment unit may obtain the information representing the kind of the scope unit received by the scope information receiving unit.

The scope unit may include a storage unit that stores the information representing the kind of the scope unit, and the scope information obtainment unit may obtain the information representing the kind of the scope unit by reading the information from the storage unit.

The image obtainment apparatus of the present invention may further include a shutter speed receiving unit that receives an input of the second constant speed, and the electronic shutter speed control unit may use the second constant speed received by the shutter speed receiving unit.

The image obtainment apparatus of the present invention may further include a user information receiving unit that receives identification information about a user, and the electronic shutter speed control unit may set the second constant speed based on the identification information about the user received by the user information receiving unit.

The electronic shutter speed control unit may obtain an up-to-latest-time history of the light amount of the illumination light output from the light source, and change the second constant speed based on the obtained up-to-latest-time latest history of the light amount.

An image obtainment method of the present invention is an image obtainment method for obtaining an image of a region to be observed by illuminating the region to be observed with illumination light output from a light source, and by imaging, by an imaging device, light output from the region to be observed by illumination with the illumination light, wherein the electronic shutter speed is controlled at a first constant speed, and the light amount of the illumination light output from the light source is controlled based on the light amount of the illumination light with which the region to be observed has been illuminated, when the light amount of the illumination light with which the region to be observed has been illuminated is less than or equal to a first threshold value, and wherein the electronic shutter speed is controlled at a speed based on the light amount of the illumination light with which the region to be observed has been illuminated, and the light amount of the illumination light output from the light source is controlled at a predetermined constant light amount, when the light amount of the illumination light with which the region to be observed has been illuminated is greater than the first threshold value and less than or equal to a second threshold value that is larger than the first threshold value, and wherein the electronic shutter speed is controlled at a second constant speed that is higher than the first constant speed, and the light amount of the illumination light output from the light source is controlled based on the light amount of the illumination light with which the region to be observed has been illuminated, when the light amount of the illumination light with which the region to be observed has been illuminated is greater than the second threshold value.

According to the image obtainment method and apparatus of the present invention, when the light amount of illumination light with which a region to be observed has been illuminated is less than or equal to a first threshold value, the electronic shutter speed is controlled at a first constant speed, and the light amount of the illumination light output from the light source is controlled based on the light amount of the illumination light with which the region to be observed has been illuminated (first control mode). Further, when the light amount of the illumination light with which the region to be observed has been illuminated is greater than the first threshold value and less than or equal to a second threshold value that is larger than the first threshold value, the electronic shutter speed is controlled at a speed based on the light amount of the illumination light with which the region to be observed has been illuminated, and the light amount of the illumination light output from the light source is controlled at a predetermined constant light amount (second control mode). Further, when the light amount of the illumination light with which the region to be observed has been illuminated is greater than the second threshold value, the electronic shutter speed is controlled at a second constant speed that is higher than the first constant speed, and the light amount of the illumination light output from the light source is controlled based on the light amount of the illumination light with which the region to be observed has been illuminated (third control mode). Therefore, it is possible to control the light amount of illumination light and the electronic shutter speed in three control modes based on the level of brightness of a region to be observed, i.e., whether the region is light or dark. Accordingly, it is possible to control the light amount of illumination light and the electronic shutter speed based on the level of brightness of the region to be observed more appropriately than the method disclosed in Patent Document 1. Hence, it is possible to more appropriately maintain a constant brightness of visible images displayed on a monitor, and to reduce a blur in still images.

Especially, in the second control mode, the light amount of illumination light is controlled at a predetermined constant light amount, and priority is given to control of the electronic shutter speed to adjust the brightness of the images. Therefore, high-response-speed control of an exposure light amount is possible without using a complicated mechanism, such as a diaphragm.

DESCRIPTION OF THE PREFERRED EMBODIMENTS

Figure 1:
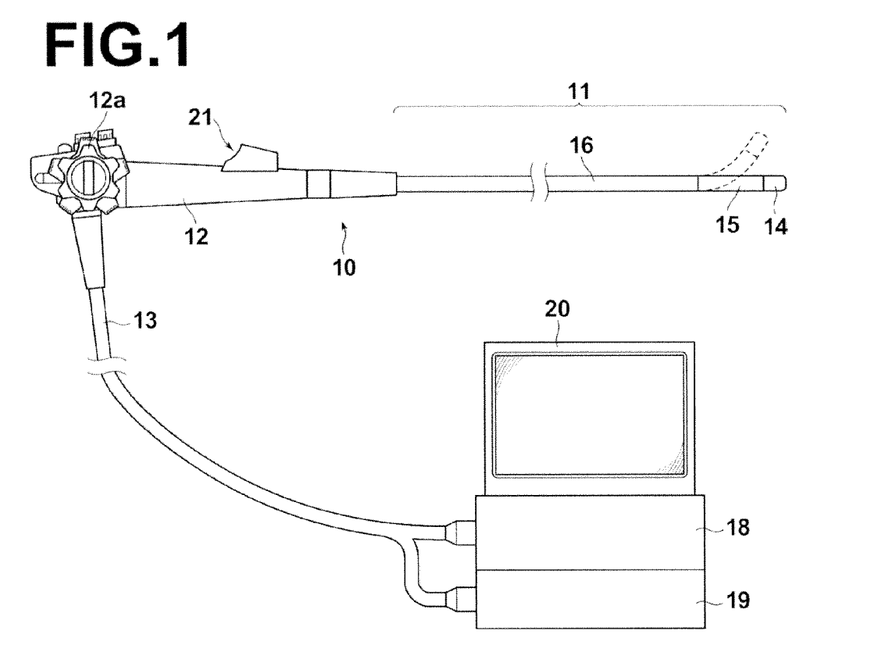
FIG. 1 is a schematic external view illustrating the structure of an endoscope system using an embodiment of an image obtainment apparatus of the present invention.

Hereinafter, an endoscope system using an embodiment of an image obtainment apparatus of the present invention will be described in detail with reference to drawings. The characteristic feature of the endoscope system of the present embodiment lies in control of the light amount of illumination light and control of the electronic shutter speed of an imaging device. First, the configuration of the whole system will be described. FIG. 1 is a schematic external view illustrating the structure of the endoscope system according to the present embodiment.

As illustrated in FIG. 1, the endoscope system of the present invention includes a scope unit 10, a universal cable 13, a processor apparatus 18, a light source apparatus 19, and a monitor 20. An end of the universal cable 13 is connected to the scope unit 10, and the other end of the universal cable 13 is connected to the processor apparatus 18 and the light source apparatus 19. The monitor 20 displays images based on image signals output from the processor apparatus 18.

The scope unit 10 includes an insertion unit 11, which is inserted into a patient's body, and an operation unit 12 for receiving a predetermined operation by an operator (user). The insertion unit 11 is tubular. Specifically, as illustrated in FIG. 1, the insertion unit 11 includes a leading-end hard portion 14, a curve portion 15, and a flexible tube portion 16, which are provided in this order from the leading end of the insertion unit 11.

The leading-end hard portion 14 is made of a hard metal material or the like. The flexible tube portion 16 connects the operation unit 12 and the curve portion 15 to each other, and the flexible tube portion 16 is a long flexible portion having a small diameter. The curve portion 15 performs a curve or bend operation when an angle wire inserted and set in the insertion unit 11 is pushed forward or pulled backward by an operation of an angle knob 12a provided in the operation unit 12. By this operation, the leading-end hard portion 14 is directed to a desirable direction in a patient's body, and a desirable region to be observed is imaged by an imaging device provided in the leading-end hard portion 14 (the imaging device will be described later). Further, the operation unit 12 includes a forceps opening 21, through which a treatment instrument or the like is inserted. The forceps opening 21 is connected to a forceps tube 26 arranged in the insertion unit 11 (the forceps tube 26 will be described later).

Figure 2:
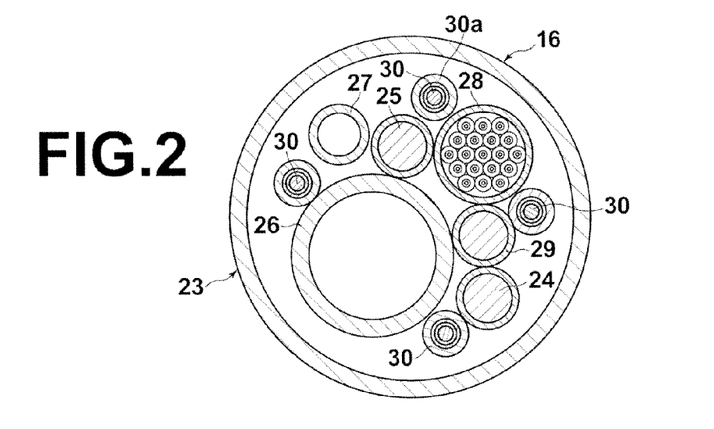
FIG. 2 is a cross section illustrating the inside of a flexible tube portion of an insertion unit.

As illustrated in FIG. 2, the flexible tube portion 16 is structured in such a manner that plural elements, such as light guides 24, 25 for guiding illumination light to a lens for illumination in the leading-end hard portion 14, the forceps tube 26, an air-supply water-supply tube 27, a multi-core cable 28, and a tube 29 for jetting 29, are movably inserted in a flexible tube 23. The multi-core cable 28 is, mainly, a bundle of wires (lines), such as a control signal wire and an image signal wire. The control signal wire is used to send control signals for driving the image device from the processor apparatus 18, and the image signal wire is used to send image signals obtained by imaging by the imaging device to the processing apparatus 18. These plural signal wires are coated with protection coating. In FIG. 2, sign 30 represents an angle wire for operating the curve portion 15, and the angle wire 30 is inserted through a close-contact coil pipe 30a.

Figure 3:
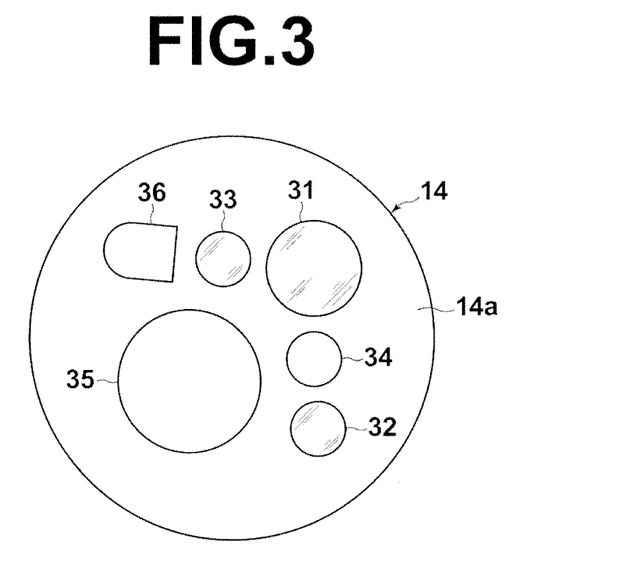
FIG. 3 is a diagram illustrating the structure of a leading end of the insertion unit.

As illustrated in FIG. 3, an observation window 31, illumination windows 32, 33, a jet opening 34 for jetting, a forceps outlet 35, an air-supply water-supply nozzle 36, and the like are provided on a leading-end surface 14a of the leading-end hard portion 14. Further, a part of an objective optical system is arranged in the observation window 31. The objective optical system is used to capture light of an image of a region to be observed in a patient's body. Further, a part of a lens for illumination is mounted on the illumination windows 32, 33, and the region to be observed in the patient's body is illuminated with illumination light that has been output from the light source apparatus 19 and guided by light guides 24, 25 through the illumination windows 32, 33. The forceps outlet 35 communicates with the forceps opening 21 provided in the operation unit 12 through the forceps tube 26. The air-supply water-supply nozzle 36 jets washing water (Liquid) or air to clean the observation window 31 by an operation of an air-supply water-supply button provided in the operation unit 12. The jet opening 34 for jetting jets fluid such as air and carbon dioxide gas, which is supplied by a gas supply apparatus, toward the region to be observed in FIG. 3, a gas-supply liquid-supply apparatus for supplying liquid or gas to be jetted from the air-supply water-supply nozzle 36, the jet opening 34 for jetting, and the like is not illustrated.

Figure 4:
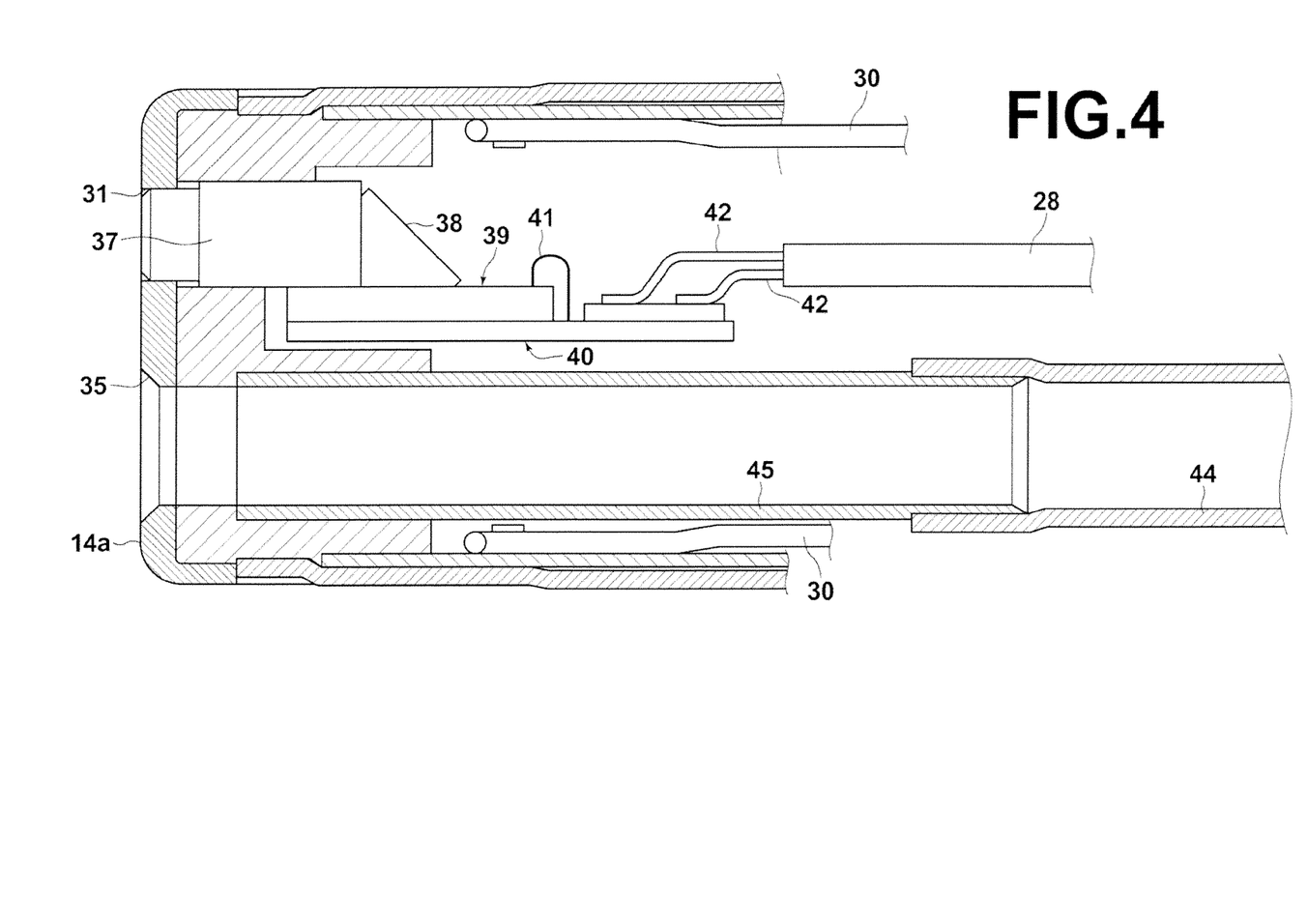
FIG. 4 is a cross section illustrating the inside of the leading end of the insertion unit.

Further, as illustrated in FIG. 4, an objective optical system 37 is arranged at a position facing the observation window 31. Illumination light output through the illumination windows 32, 33 is reflected at the region to be observed, and enters the observation window 31. An image of the region to be observed, which has entered through the observation window 31, enters a prism 38 through the objective optical system 37. The image is refracted in the prism 38, and an image is formed on an imaging surface of an imaging device 39.

The imaging device 39 performs photoelectric conversion on the image formed on the imaging surface, and outputs image signals. Further, a color filter of three primary colors, i.e., red (R), green (G), and blue (B), in Bayer arrangement or honeycomb arrangement is provided on the imaging surface of the imaging device 39.

The imaging device 39 outputs an image signal for each frame based on a predetermined synchronous signal output from the control unit 56 in the processor apparatus 18. Further, the imaging device 39 has an electronic shutter function, and the shutter speed of the electronic shutter is controlled by an electronic shutter speed control unit 58 in the processor apparatus 18 (the electronic shutter speed control unit 58 will be described later)

For example, a CCD (Charge-Coupled Device) sensor, a CMOS (Complementary Metal Oxide Semiconductor) sensor, and the like are used as the imaging device 39. In the present embodiment, the imaging device 39 is a so-called bare chip, which is a chip before packaging, and electrodes on the chip are connected to wire patterns (wiring patterns) on a circuit board (substrate) 40 through a connection line 41 by using a method, such as wire bonding, TAB (tape automated bonding), and flip chip.

Further, wire patterns for sending a control signal to be input to the imaging device 39 and an image signal output from the imaging device 39 to a control signal wire and an image signal wire in the multi-core cable 28 are formed on the circuit board 40 (hereinafter, the control signal wire and the image signal wire will be collectively referred to as signal wires).

Plural signal wires 42 are exposed from an end of the multi-core cable 28 arranged parallel to the longitudinal direction of the insertion unit 11. The plural signal wires 42 are electrically connected to the wire patterns on the circuit board 40.

Further, a flexible tube 44 made of synthetic resin is arranged in the curve portion 15. An end of the flexible tube 44 is connected to the forceps tube 26, and the other end of the flexible tube 44 is connected to a hard tube 45 arranged in the leading-end hard portion 14. The hard tube 45 is fixed in the leading-end hard portion 14, and the leading end of the hard tube 45 is connected to the forceps outlet 35.

Figure 5:
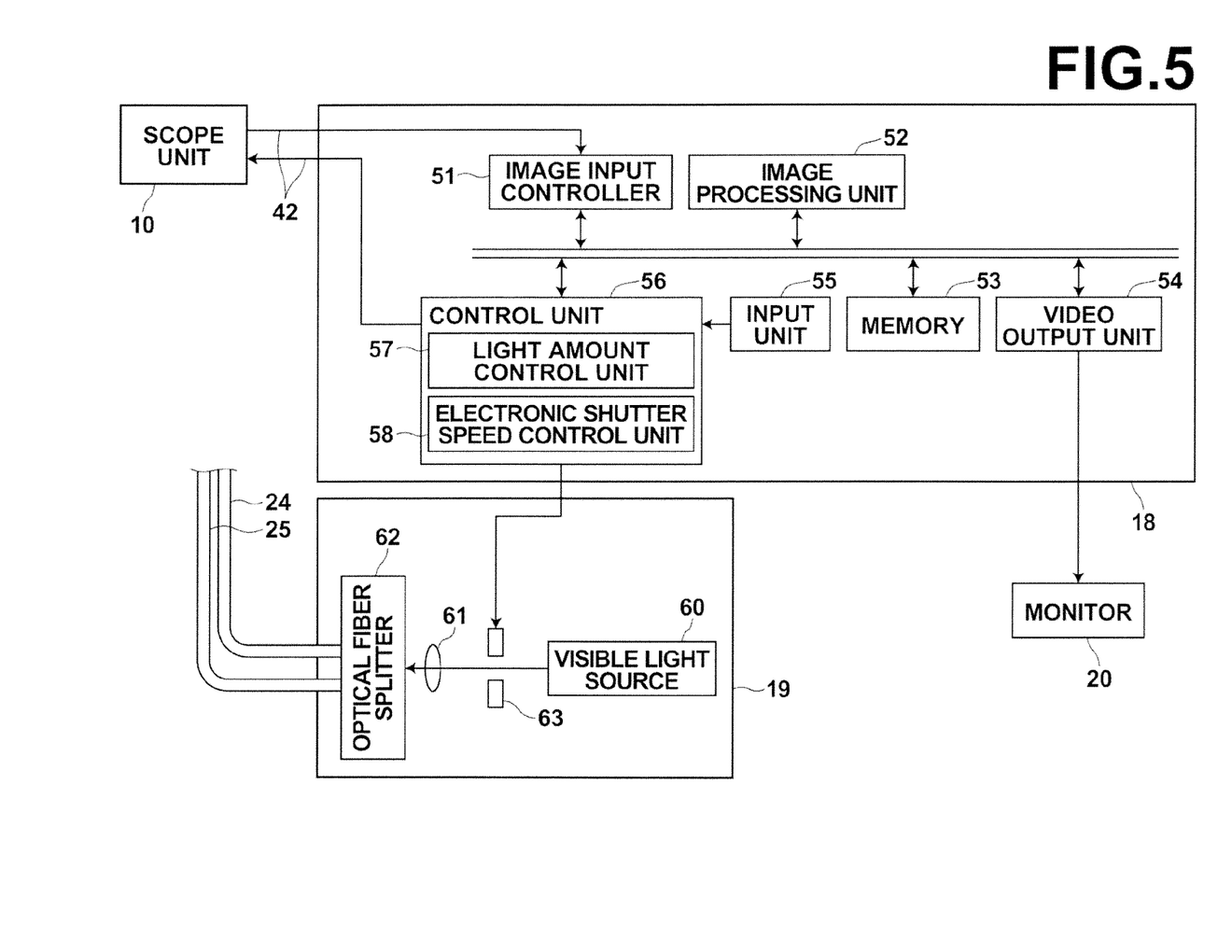
FIG. 5 is a block diagram illustrating the internal configuration of a processor apparatus and a light source apparatus in the endoscope system illustrated in FIG. 1.

FIG. 5 is a schematic diagram illustrating the internal configuration of the processor apparatus 18 and the light source apparatus 19. As illustrated in FIG. 5, the processor apparatus 18 includes an image input controller 51, an image processing unit 52, a memory 53, a video output unit 54, an input unit 55 and a control unit 56.

The image input controller 51 includes a line buffer having a predetermined capacity, and temporarily stores an image signal for each frame output from the imaging device 39 in the scope unit 10. The image signal stored in the image input controller 51 is stored in the memory 53 through a bus.

The image processing unit 52 receives the image signal for each frame that has been read out from the memory 53. The image processing unit 52 performs predetermined image processing on the image signals, and outputs the processed image signals to a bus.

The video output unit 54 receives, through the bus, the image signal that has been output from the image processing unit 52, and generates a display control signal by performing predetermined processing on the received image signal. Further, the video output unit 54 outputs the display control signal to the monitor 20.

The input unit 55 receives an input, such as a predetermined operation instruction and a control parameter, by an operator or user. Particularly, in the present embodiment, the input unit 55 receives information representing the kind of the scope unit 10, and an input of setting of the electronic shutter speed of the imaging device 39 in the scope unit 10.

The control unit 56 controls the whole system. Particularly, in the present embodiment, the control unit 56 includes a light amount control unit 57, and an electronic shutter speed control unit 58. The light amount control unit 57 controls the light amount of illumination light entering the light guides 24, 25 in the scope unit 10 by controlling the stop amount of an aperture 63 (a degree of narrowing the aperture) in the light source apparatus 19. The electronic shutter speed control unit 58 controls the electronic shutter speed of the imaging device 39 in the scope unit 10.

The light amount control unit 57 and the electronic shutter speed control unit 58 control the stop amount of the aperture 63 and the electronic shutter speed of the imaging device 39, respectively, based on the value of a luminance signal generated from the image signal obtained by imaging by the imaging device 39. The control methods will be described later in detail.

As illustrated in FIG. 5, the light source apparatus 19 includes a visible light source 60, a condensing lens 61, an optical fiber splitter 62, and the aperture 63. The visible light source 60 outputs illumination light. The condensing lens 61 condenses the illumination light output from the visible light source 60, and makes the condensed illumination light enter the optical fiber splitter 62. The optical fiber splitter 62 makes the illumination light that has been input by the condensing lens 61 enter both of the light guides 24, 25 simultaneously. The aperture 63 controls, based on a control signal output from the light amount control unit 57 in the processor apparatus 18, the light amount of the illumination light that has been output from the visible light source 60 so that the illumination light after control enters the light guides 24, 25.

As the visible light source 60, a halogen lamp may be used for example. The wavelength range of white light output from the halogen lamp is from 400 nm to 1800 nm.

Next, the action of an endoscope system according to the present invention will be described.

First, the scope unit 10 is mounted on the processor apparatus 18 and the light source apparatus 19 through a universal cable 13.

The insertion unit 11 of the scope unit 10 is inserted into a patient's body, and the leading end of the insertion unit 11 is placed in the vicinity of a region to be observed. Further, a visible image is obtained by imaging, and the obtained image is displayed.

Specifically, illumination light output from the visible light source 60 in the light source apparatus 19 simultaneously enters both of the light guides 24, 25 in the universal cable 13 through the condensing lens 61 and the optical fiber splitter 62. It is assumed that the stop amount of the aperture 63 in an initial state is set at a predetermined amount in advance.

The illumination light that has entered the light guides 24, 25 in the universal cable 13 is guided to the leading end of the insertion unit 11 by the light guides 24, 25 in the insertion unit 11. Further, the illumination light is output from illumination windows 32, 33 provided at the leading end of the insertion unit 11, and illuminates the region to be observed in the patient's body.

When the region to be observed is illuminated with the illumination light, an image is reflected from the region to be observed. The reflected image enters the insertion unit 11 through the observation window 31 at the leading end of the insertion unit 11. After light representing the image enters a prism 38 through an objective optical system 37, the light is refracted in the prism 38. According, an image is formed on the imaging surface of the imaging device 39, and the image is captured by the imaging device 39.

The imaging device 39 sequentially outputs an image signal for each frame based on a predetermined synchronous signal output from the control unit 56 in the processor apparatus 18. Further, it is assumed that the electronic shutter speed of the imaging device 39 in an initial state is set in advance.

Further, predetermined circuits provided on the circuit board 40 perform CDS/AGC (correlated double sampling/automatic gain control) processing, A/D (analog to digital) conversion processing and the like on image signals of R, G and B that have been obtained by the imaging device 39. The processed image signals are input to the processor apparatus 18 through the insertion unit 11 and the multi-core cable 28 in the universal cable 13.

Further, the image signal of R, G and B that has been input to the processor apparatus 18 is temporarily stored in the image input controller, and stored in the memory 53. Further, an image signal for each frame is read out from the memory 53, and the image processing unit 52 performs graduation correction processing and sharpness correction processing on the image signal. The processed image signals are sequentially output to the video output unit 54.

The video output unit 54 performs predetermined processing on the input image signals, and generates display control signals. The video output unit 54 sequentially outputs a display control signal for each frame to the monitor 20. The monitor 20 displays a visible image based on the input display control signal.

Here, when a visible image of the region to be observed is obtained by imaging as described above, short-distance imaging (close-up), long-distance imaging (distant view), and the like are performed. In the short-distance imaging, the leading end of the insertion unit 11 is placed close to a lesion or the like, and imaging is performed. In the long-distance imaging, a relatively wide range including the lesion and the vicinity the lesion is imaged. In the short distance imaging, the leading end of the insertion unit 11 and the lesion are close to each other. Therefore, signals representing relatively bright images are obtained. In contrast, in the long-distance imaging, for example, when the inside of an intestine is imaged, signals representing relatively dark images are obtained, because the target of imaging is tubular.

Therefore, in the endoscope system of the present embodiment, the light amount control unit 57 generates luminance signals based on the image signals output from the scope unit 10, and adjusts the stop amount of the aperture 63 in the light source apparatus 19 based on the values of the luminance signals so that the brightness of the visible image displayed on the monitor 20 is constant. Specifically, the stop amount of the aperture 63 is controlled to a larger value, in other words, the aperture is smaller, as the value of the luminance signal is larger.

However, the range of the light amount of illumination light that is adjustable by the aperture 63 is limited because of the maximum light amount of the visible light source 60 and the mechanical precision and accuracy of the aperture 63. Therefore, it is impossible to maintain a constant brightness of visible images in some cases.

Further, in the endoscope system, a dynamic image (video image) is obtained by performing real-time imaging by the scope unit 10 as described above. Further, a still image is also obtainable by obtaining an image of a desirable frame from the visible image for each frame obtained by dynamic imaging. The still image is obtained especially to observe the region to be observed in detail. Therefore, it is desirable that a blur in the still image is minimized. Hence, it is desirable that the electronic shutter speed of the imaging device 39 is as fast as possible.

For that purpose, in the endoscope system of the present embodiment, the stop amount of the aperture 63 in the light source apparatus 19 is controlled based on the luminance signal generated from the image signal output from the scope unit 10. Further, the electronic shutter speed of the imaging device 39 in the scope unit 10 is also controlled to adjust the brightness of the visible image.

Figure 6:
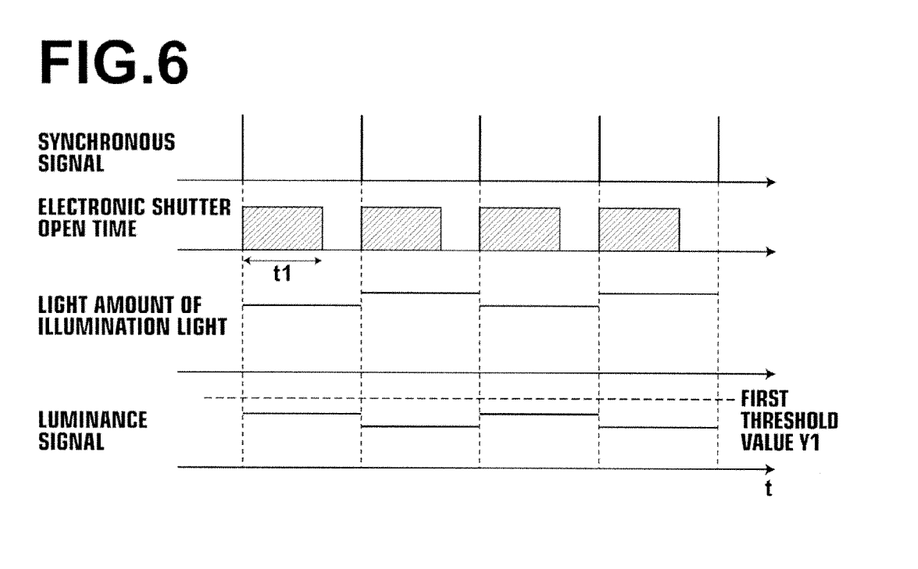
FIG. 6 is a timing chart for explaining a first control mode for controlling the light amount of illumination light and an electronic shutter speed in the endoscope system illustrated in FIG. 1.
Figure 7:
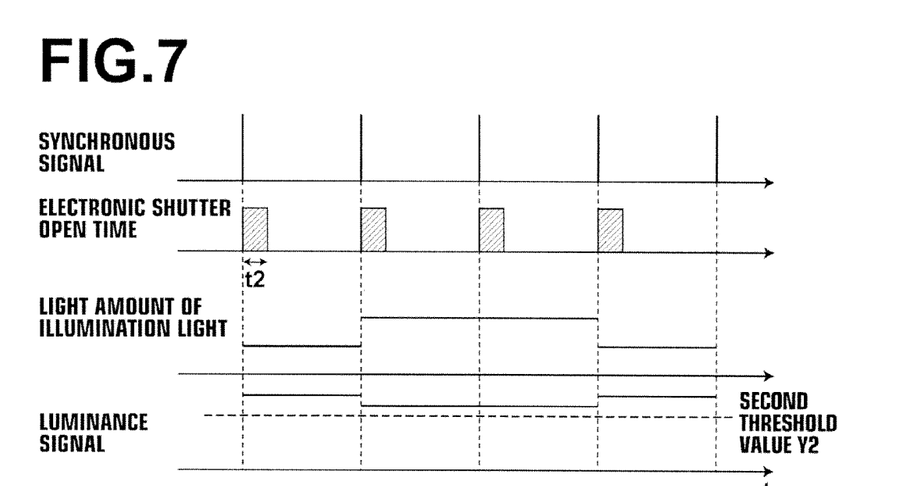
FIG. 7 is a timing chart for explaining a third control mode for controlling the light amount of illumination light and an electronic shutter speed in the endoscope system illustrated in FIG. 1.
Figure 8:
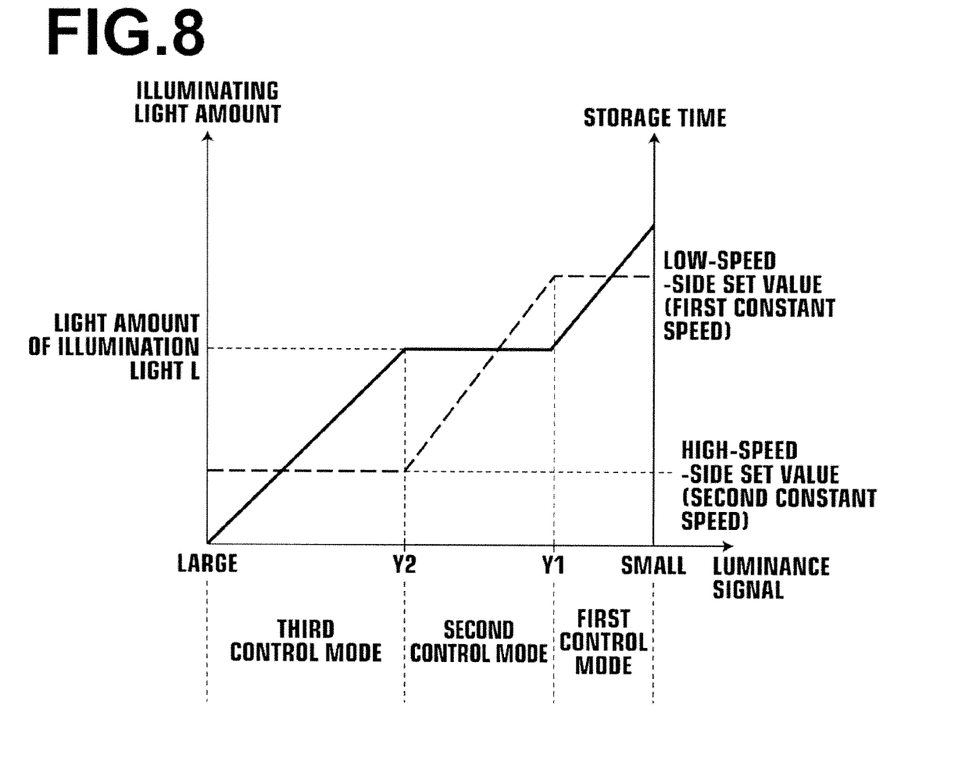
FIG. 8 is a graph illustrating control of the light amount of illumination light and control of an electronic shutter speed in first through three control modes.

Next, specific methods for controlling the stop amount of the aperture 63 in the light source apparatus 19 and the electronic shutter speed of the imaging device 39 in the scope unit 10 in the endoscope system of the present embodiment will be described with reference to the timing charts illustrated in FIGS. 6 and 7 and the graph illustrated in FIG. 8. FIGS. 6 and 7 illustrate synchronous signals used when each frame is imaged by the imaging device 39, an electronic shutter open time period (charge storage time) for each frame, and the light amount of illumination light adjusted by the aperture 63. Further, in the graph illustrated in FIG. 8, a solid line represents the light amount of illumination light with respect to the value of a luminance signal. Further, a broken line in FIG. 8 represents the electronic shutter speed with respect to the value of the luminance signal. In FIG. 8, values on the axis representing luminance signals are smaller toward the right side, and larger toward the left side.

First, as illustrated in FIG. 6, when the luminance signal generated based on the image signal output from the imaging device 39 in the scope unit 10 is less than or equal to predetermined first threshold value Y1, in other words, when an image obtained by imaging by the imaging device 39 is relatively dark, the electronic shutter speed control unit 58 and the light amount control unit 57 control the electronic shutter speed and the stop amount (the light amount of illumination light) in first control mode illustrated in FIG. 8.

Specifically, in the first control mode, the electronic shutter speed control unit 58 sets the electronic shutter speed of the imaging device 39 to a first constant speed, which is a low speed. Further, the light amount control unit 57 sets the stop amount so that the light amount of illumination light becomes appropriate based on the value of the luminance signal. It is desirable that the first constant speed of the electronic shutter speed is the lowest electronic shutter speed of all speeds at which the imaging device 39 can operate normally. However, the first constant speed of the electronic shutter speed is not limited to such a speed. Further, the first constant speed should not be lower than a frame rate (for example, ¹⁄₆₀ second). In FIG. 6, electronic shutter open time when the electronic shutter speed is the first constant speed is represented by t1. Further, the expression "sets the stop amount so that the light amount of illumination light is appropriate based on the value of the luminance signal" means that the stop amount is increased so that the light amount of illumination light becomes smaller as the value of the luminance signal is larger.

Next, as illustrated in FIG. 7, when the luminance signal generated based on the image signal output from the imaging device 39 in the scope unit 10 is larger than predetermined second threshold value Y2, in other words, when an image obtained by imaging by the imaging device 39 is relatively bright, the electronic shutter speed control unit 58 and the light amount control unit 57 control the electronic shutter speed and the stop amount (the light amount of illumination light) in third control mode illustrated in FIG. 8. As illustrated in FIG. 8, the second threshold value Y2 is larger than the first threshold value Y1.

Specifically, in the third control mode, the electronic shutter speed control unit 58 sets the electronic shutter speed of the imaging device 39 to a second constant speed, which is a high speed. Further, the light amount control unit 57 sets the stop amount so that the light amount of illumination light becomes appropriate based on the value of the luminance signal. It is desirable that the second constant speed of the electronic shutter speed is the highest electronic shutter speed of all speeds at which the imaging device 39 can operate normally. However, the second constant speed of the electronic shutter speed is not limited to such a speed. In FIG. 7, electronic shutter open time when the electronic shutter speed is the second constant speed is represented by t2. The electronic shutter open time is, for example, 1/300 second. When the electronic shutter speed is at a high speed as in this case, it is possible to reduce a blur in a still image.

Further, the expression "sets the stop amount so that the light amount of illumination light becomes appropriate based on the value of the luminance signal" means that the stop amount is increased so that the light amount of illumination light becomes smaller as the value of the luminance signal is larger.

Next, when the luminance signal generated based on the image signal output from the imaging device 39 in the scope unit 10 is larger than the first threshold value Y1 and less than or equal to the second threshold value Y2, in other words, when the brightness of an image obtained by imaging by the imaging device 39 is in the range between the brightness in the first control mode and the brightness in the second control mode, the electronic shutter speed control unit 58 and the light amount control unit 57 control the electronic shutter speed and the stop amount (the light amount of illumination light) in second control mode illustrated in FIG. 8.

Specifically, in the second control mode, the electronic shutter speed control unit 58 sets the electronic shutter speed of the imaging device 39 to a speed based on the value of the luminance signal (for example, 1/60 second through 1/300 second). Further, the light amount control unit 57 sets the stop amount so that the light amount of illumination light becomes constant light amount L. The constant light amount L is set in advance. Further, the expression "sets the electronic shutter speed of the imaging device 39 to a speed based on the value of the luminance signal" means that the electronic shutter speed is set higher as the value of the luminance signal is larger.

As described above, in the second control mode, priority is given to control of the electronic shutter speed than control of the light amount of illumination light, and the electronic shutter speed is increased as high as possible. Therefore, it is possible to minimize a blur in the still image.

Further, in the second control mode, the light amount of illumination light is controlled at a predetermined constant light amount, and priority is given to control of the electronic shutter speed to control the brightness of images. Therefore, it is possible to easily perform high-response-speed control of exposure light amounts without using a diaphragm or the like having a complicated mechanism. Further, it is possible to accurately estimate a rise in temperature caused by heat generation at the leading end of the insertion unit 11, compared with a case of changing the light amount by frequently changing the aperture.

According to the endoscope system of the aforementioned embodiment, the light amount of illumination light and the electronic shutter speed are controlled in the first through third control modes based on the brightness of the region to be observed. Therefore, it is possible to control the light amount of illumination light and the electronic shutter speed based on the brightness of the region to be observed more appropriately than a conventional system. Further, it is possible to more appropriately maintain a constant brightness of visible images displayed on the monitor. Further, it is possible to reduce a blur in a still image.

In the aforementioned embodiment, the stop amount of the aperture 63 was controlled to adjust the light amount of the illumination light. However, when a semiconductor laser diode or the like is used as the visible light source instead of the halogen lamp, a drive electric current supplied to the semiconductor laser diode should be controlled.

Further, in the aforementioned embodiment, the light amount of illumination light in the second control mode is controlled at constant light amount L that has been set in advance. However, the constant light amount L may be changed. Specifically, the light amount control unit 57 may obtain a history of the light amount of illumination light in a predetermined time period (for example, one minute) up to a time point immediately before obtainment of the history (up-to-latest-time history), and change the constant light amount based on the obtained history of the light amount. As the history of the light amount, for example, a cumulative value of the stop amount of the aperture 63 till a time point immediately before obtainment of the history, a cumulative value of drive electric current of the semiconductor laser diode till a time point immediately before obtainment of the history, and the like may be used. When the cumulative value of the stop amount is less than or equal to a predetermined threshold value, or when the cumulative value of the drive electric current of the semiconductor laser diode is greater than or equal to a predetermined threshold value, the constant light amount L should be controlled to a lower value. When the constant light amount L is reduced, it is possible to suppress a rise in temperature by heat generation at the leading end of the insertion unit 11 in the scope unit 10.

Alternatively, the electronic shutter speed control unit 58 may obtain a history of the light amount of illumination light as described above. Further, the second constant speed in the third control mode may be changed based on the obtained history of the light amount. Specifically, when the cumulative value of the stop amount is less than or equal to a predetermined threshold value, or when the cumulative value of the drive electric current of the semiconductor laser diode is greater than or equal to a predetermined threshold value, in other words, when the brightness of images obtained by the imaging device 39 during a predetermined time period till a time point immediately before obtainment of the history is relatively dark, the second constant speed may be controlled to a lower speed. Specifically, the electronic shutter open time t2 illustrated in FIG. 7 may be increased. Accordingly, it is possible to obtain visible images of more appropriate brightness.

Further, various kinds of scope unit 10 are used, depending on the purpose of examination or the like. Therefore, the apparatus of the present invention may be structured in such a manner that plural kinds of scope unit 10 are attachable to the processor apparatus 18 and the light source apparatus 19, and detachable therefrom.

When the apparatus is structured in such a manner, the electronic shutter speed at which the imaging device 39 can operate normally differs depending on the kind of the scope unit 10. Further, the maximum input light amount differs depending on the kind of the scope unit 10. Here, the term "maximum input light amount" means the maximum value of the light amount of light that can enter the scope unit 10, and which is set in advance based on the heat generation amount of an optical system of the scope unit 10 or the like.

Figure 9:
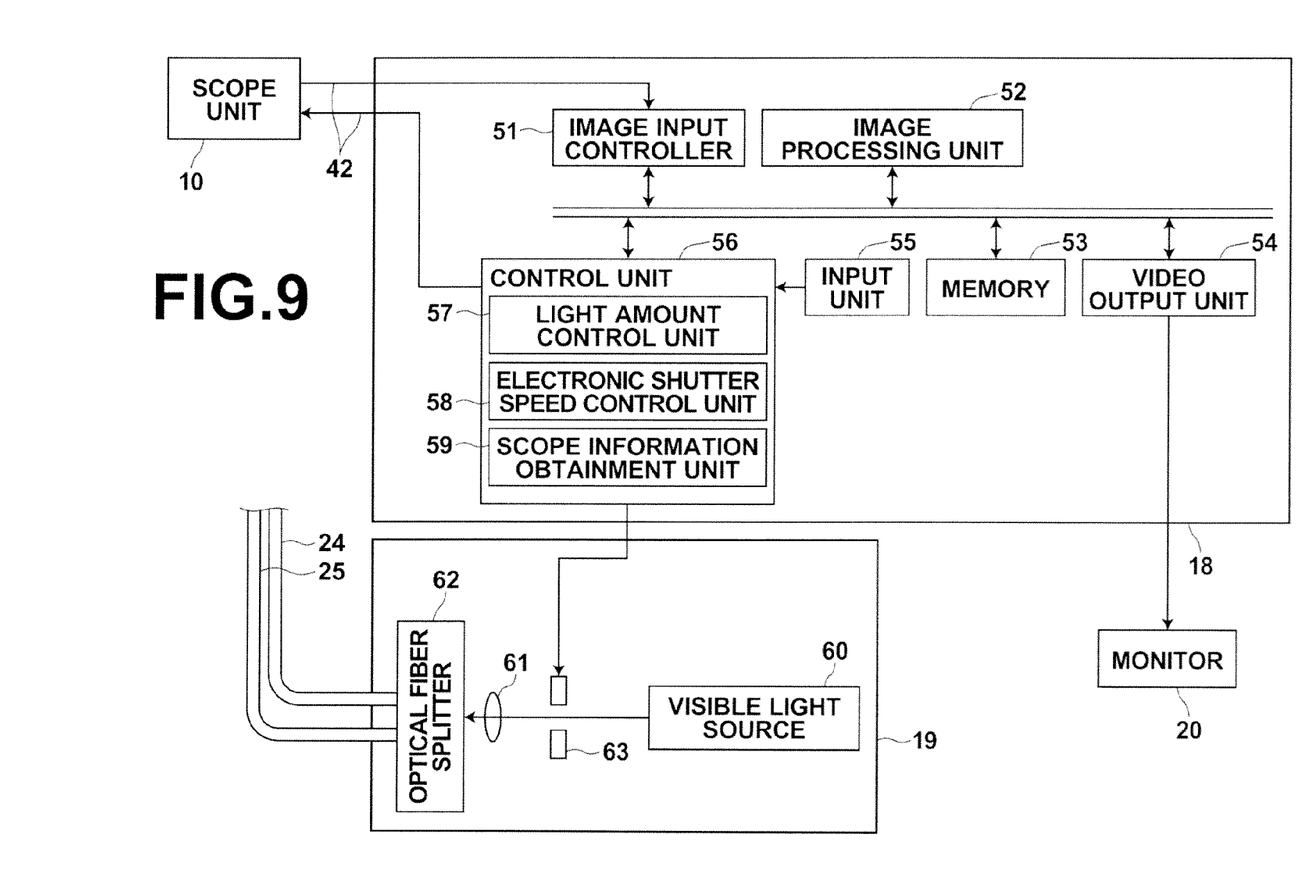
FIG. 9 is a block diagram illustrating the internal configuration of a processor apparatus and a light source apparatus in an endoscope system using another embodiment of the image obtainment apparatus of the present invention.
Figure 10:
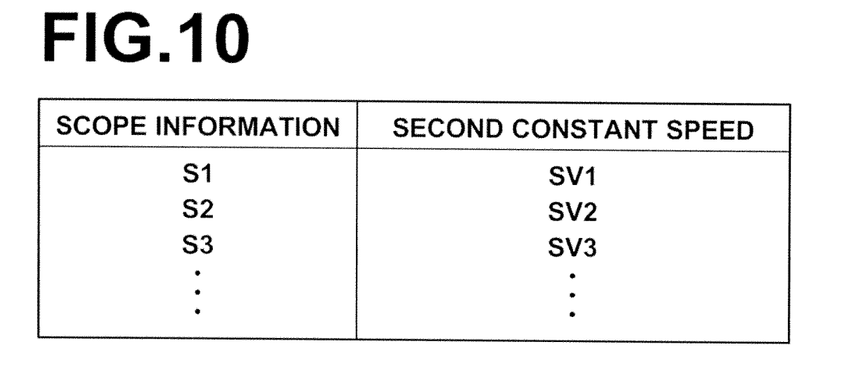
FIG. 10 is a diagram illustrating an example of a table showing correspondence between scope information and electronic shutter speed (second constant speed) in the third control mode.

Therefore, as illustrated in FIG. 9, a scope information obtainment unit 59 may be provided in the control unit 56 in the processor apparatus 18. The scope information obtainment unit 59 obtains information representing the kind of the scope unit 10. The electronic shutter speed control unit 58 may set the second constant speed in the third control mode based on the information representing the kind of the scope unit 10 obtained by the scope information obtainment unit 59. Specifically, for example, a correspondence table as illustrated in FIG. 10 may be set in the electronic shutter speed control unit 58. The correspondence table illustrated in FIG. 10 shows correspondence between scope information (S1, S2, S3 . . . ) of the scope unit 10 and second constant speed (SV1, SV2, SV3 . . . ). Further, the electronic shutter speed control unit 58 may set the second constant speed based on the scope information obtained by the scope information obtainment unit 59 and the table. Further, as the second constant speed set in the table, the highest electronic shutter speed of electronic shutter speeds of the imaging device 39 provided in each of the scope units 10 should be set. Further, when the second constant speed is set based on the maximum input light amount of light entering each scope unit 10, the second constant speed should be increased as the maximum input light amount is larger.

Further, the information representing the kind of the scope unit 10 may be information representing the kind of the scope unit 10, itself. Alternatively, the information representing the kind of the scope unit 10 may be information representing the kind of an imaging device provided in the scope unit 10, or information representing the maximum input light amount of the scope unit 10.

For example, the information representing the kind of the scope unit 10 may be set or input by a user by using an input unit 55. Further, the scope information obtainment unit 59 should obtain the information representing the kind of the scope unit that has been received at the input unit 55.

Figure 11:
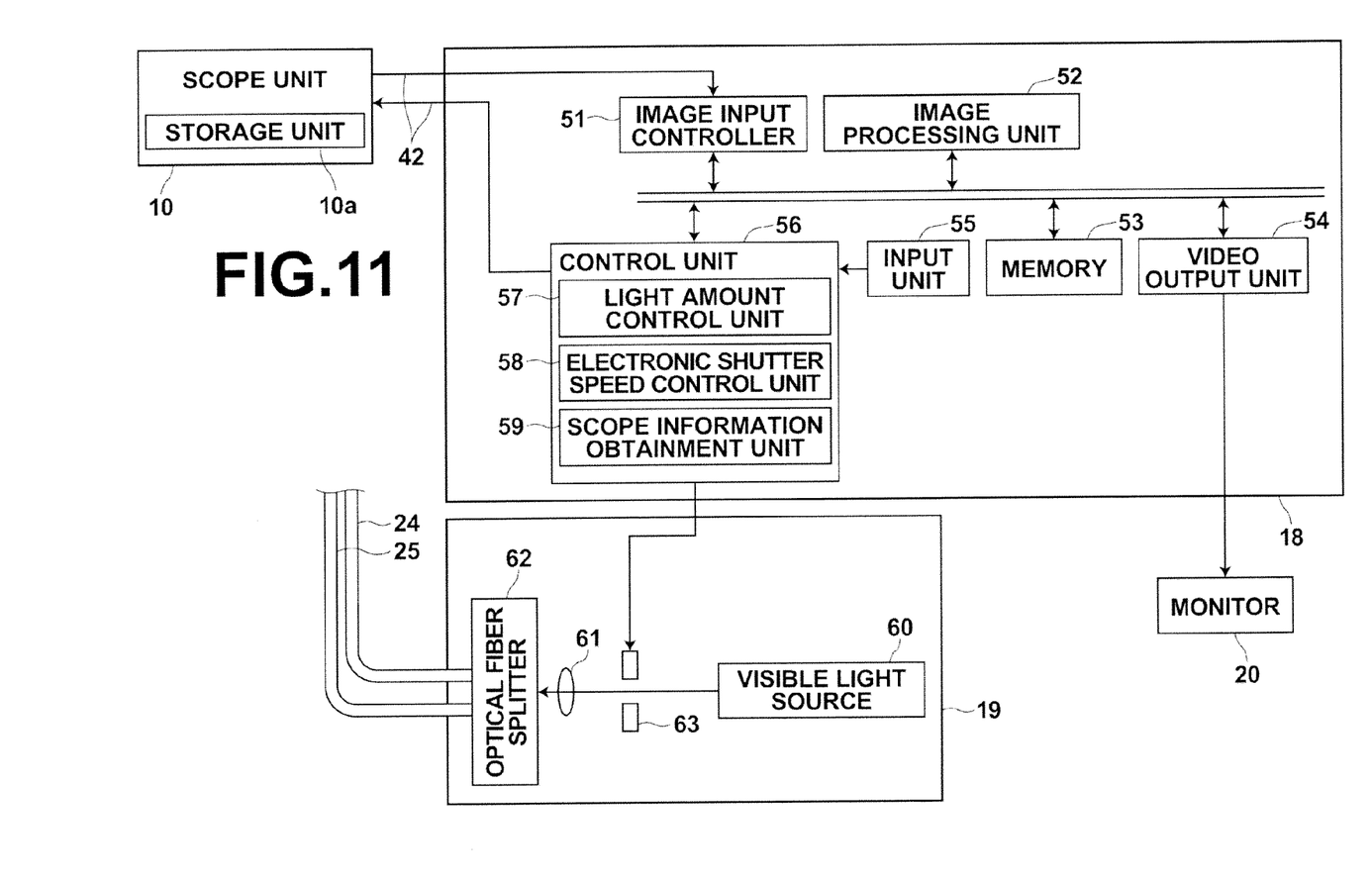
FIG. 11 is a block diagram illustrating the internal configuration of a processor apparatus and a light source apparatus in an endoscope system using another embodiment of the image obtainment apparatus of the present invention.

Alternatively, as illustrated in FIG. 11, a storage unit 10a that stores information representing the kind of the scope unit 10 may be provided in the scope unit 10. Further, the scope information obtainment unit 59 may obtain the information representing the kind of the scope unit by reading out the information from the storage unit 10a.

Further, since the second constant speed in the third control mode is set at a relatively high speed, when a dynamic image (video) is obtained by imaging, visible images do not change smoothly in some cases. Consequently, a video image composed of successive frames that are not sufficiently close to each other is generated, and the video image does not move smoothly in some cases. Further, some users may not like such conditions.

Figure 12:
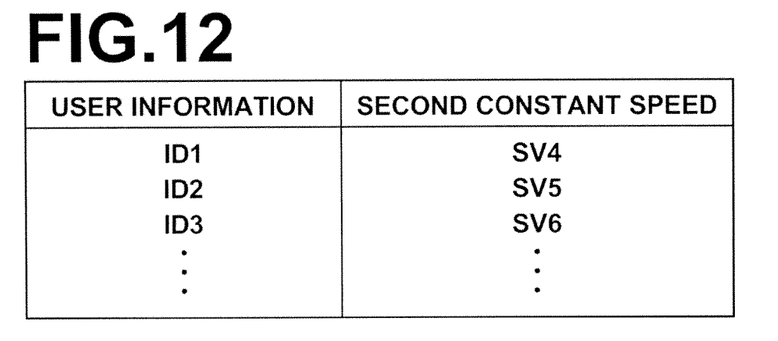
FIG. 12 is a diagram illustrating an example of a table showing correspondence between user identification information and electronic shutter speed (second constant speed) in the third control mode.

Therefore, the second constant speed in the third control mode may be provided in such a manner that a user can input and set an arbitrary speed by using the input unit 55. Alternatively, for example, a correspondence table as illustrated in FIG. 12 may be set in the electronic shutter speed control unit 58. The correspondence table illustrated in FIG. 12 shows a correspondence between identification information (ID1, ID2, ID3 . . . ) about users and second constant speed (SV4, SV5, SV6 . . . ). Further, the electronic shutter speed control unit 58 may set, as the second constant speed, a speed that suits the preference of each user by setting the second constant speed based on identification information about a user that has been input and set at the input unit 55 and information in the aforementioned table.

What is claimed is:

1. An image obtainment apparatus comprising:
   an illumination light illuminating unit that illuminates a region to be observed with illumination light output from a light source;
   an image obtainment unit that obtains an image of the region to be observed by imaging, by an imaging device, light output from the region to be observed by illumination with the illumination light;
   a light amount control unit that controls the light amount of the illumination light output from the light source; and
   an electronic shutter speed control unit that controls the electronic shutter speed of the imaging device,
   wherein the electronic shutter speed control unit controls the electronic shutter speed at a first constant speed, and the light amount control unit controls the light amount of the illumination light output from the light source based on the light amount of the illumination light with which the region to be observed has been illuminated, when the light amount of the illumination light with which the region to be observed has been illuminated is less than or equal to a first threshold value, and
   wherein the electronic shutter speed control unit controls the electronic shutter speed at a speed based on the light amount of the illumination light with which the region to be observed has been illuminated, and the light amount control unit controls the light amount of the illumination light output from the light source at a predetermined constant light amount, when the light amount of the illumination light with which the region to be observed has been illuminated is greater than the first threshold value and less than or equal to a second threshold value that is larger than the first threshold value, and
   wherein the electronic shutter speed control unit controls the electronic shutter speed at a second constant speed that is higher than the first constant speed, and the light amount control unit controls the light amount of the illumination light output from the light source based on the light amount of the illumination light with which the region to be observed has been illuminated, when the light amount of the illumination light with which the region to be observed has been illuminated is greater than the second threshold value.

2. An image obtainment apparatus, as defined in claim 1, wherein the light amount control unit obtains an up-to-latest-time history of the light amount of the illumination light output from the light source, and changes the predetermined constant light amount based on the obtained up-to-latest-time history of the light amount.

3. An image obtainment apparatus, as defined in claim 1, the apparatus further comprising:
   a scope unit that is inserted into a patient's body to guide the illumination light output from the light source to illuminate the region to be observed with the illumination light, and to receive the light output from the region to be observed, and the scope unit being provided in a detachable manner; and a scope information obtainment unit that obtains information representing the kind of the scope unit, wherein the electronic shutter speed control unit sets the second constant speed based on the information representing the kind of the scope unit obtained by the scope information obtainment unit.

4. An image obtainment apparatus, as defined in claim 3, wherein the information representing the kind of the scope unit includes information representing the kind of the imaging device.

5. An image obtainment apparatus, as defined in claim 3, wherein the information representing the kind of the scope unit includes information about the maximum light amount of the illumination light that is receivable by the scope unit.

6. An image obtainment apparatus, as defined in claim 3, the apparatus further comprising:

a scope information receiving unit that receives an input of the information representing the kind of the scope unit, wherein the scope information obtainment unit obtains the information representing the kind of the scope unit received by the scope information receiving unit.

7. An image obtainment apparatus, as defined in claim 3, wherein the scope unit includes a storage unit that stores the information representing the kind of the scope unit, and wherein the scope information obtainment unit obtains the information representing the kind of the scope unit by reading the information from the storage unit.

8. An image obtainment apparatus, as defined in claim 1, the apparatus further comprising:

a shutter speed receiving unit that receives an input of the second constant speed, wherein the electronic shutter speed control unit uses the second constant speed received by the shutter speed receiving unit.

9. An image obtainment apparatus, as defined in claim 1, the apparatus further comprising:

a user information receiving unit that receives identification information about a user, wherein the electronic shutter speed control unit sets the second constant speed based on the identification information about the user received by the user information receiving unit.

10. An image obtainment apparatus, as defined in claim 1, wherein the electronic shutter speed control unit obtains an up-to-latest-time history of the light amount of the illumination light output from the light source, and changes the second constant speed based on the obtained up-to-latest-time history of the light amount.

11. An image obtainment method for obtaining an image of a region to be observed by illuminating the region to be observed with illumination light output from a light source, and by imaging, by an imaging device, light output from the region to be observed by illumination with the illumination light, wherein the electronic shutter speed is controlled at a first constant speed, and the light amount of the illumination light output from the light source is controlled based on the light amount of the illumination light with which the region to be observed has been illuminated, when the light amount of the illumination light with which the region to be observed has been illuminated is less than or equal to a first threshold value, and wherein the electronic shutter speed is controlled at a speed based on the light amount of the illumination light with which the region to be observed has been illuminated, and the light amount of the illumination light output from the light source is controlled at a predetermined constant light amount, when the light amount of the illumination light with which the region to be observed has been illuminated is greater than the first threshold value and less than or equal to a second threshold value that is larger than the first threshold value, and wherein the electronic shutter speed is controlled at a second constant speed that is higher than the first constant speed, and the light amount of the illumination light output from the light source is controlled based on the light amount of the illumination light with which the region to be observed has been illuminated, when the light amount of the illumination light with which the region to be observed has been illuminated is greater than the second threshold value.

* * * * *